(12) United States Patent
Parker

(10) Patent No.: US 8,216,287 B2
(45) Date of Patent: *Jul. 10, 2012

(54) TANGENTIAL FORCE RESISTANT COUPLING FOR A PROSTHETIC DEVICE

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 997 days.

This patent is subject to a terminal disclaimer.

(21) Appl. No.: 12/167,851

(22) Filed: Jul. 3, 2008

(65) Prior Publication Data

US 2009/0248086 A1 Oct. 1, 2009

Related U.S. Application Data

(60) Provisional application No. 61/041,185, filed on Mar. 31, 2008.

(51) Int. Cl.
*A61B 17/84* (2006.01)
*H04R 25/00* (2006.01)
(52) U.S. Cl. ............... 606/300; 381/326; 600/25
(58) Field of Classification Search .......... 606/300–301; 600/25; 381/326
See application file for complete search history.

(56) References Cited

U.S. PATENT DOCUMENTS

| | | | |
|---|---|---|---|
| 5,735,790 A | 4/1998 | Håkansson et al. | |
| 5,935,170 A | 8/1999 | Håkansson et al. | |
| 7,021,676 B2 | 4/2006 | Westerkull et al. | |
| 7,065,223 B2 | 6/2006 | Westerkull et al. | |
| 7,116,794 B2 | 10/2006 | Westerkull et al. | |
| 7,198,596 B2 | 4/2007 | Westerkull et al. | |
| 7,874,977 B2 * | 1/2011 | Pitulia | 600/23 |
| 2004/0210103 A1 * | 10/2004 | Westerkull | 600/25 |
| 2005/0248158 A1 | 11/2005 | Westerkull | |
| 2006/0025648 A1 | 2/2006 | Lupin et al. | |
| 2009/0192345 A1 | 7/2009 | Westerkull et al. | |
| 2009/0245554 A1 | 10/2009 | Parker | |
| 2009/0248023 A1 | 10/2009 | Parker | |
| 2010/0292529 A1 * | 11/2010 | Westerkull et al. | 600/25 |
| 2011/0268303 A1 | 11/2011 | Ahsani | |

FOREIGN PATENT DOCUMENTS

| | | |
|---|---|---|
| EP | 0996391 | 5/2000 |
| WO | 0209622 | 2/2002 |
| WO | 03001845 | 1/2003 |
| WO | 03001846 | 1/2003 |
| WO | 2004105650 | 12/2004 |

* cited by examiner

*Primary Examiner* — Nicholas Woodall
(74) *Attorney, Agent, or Firm* — Kilpatrick, Townsend & Stockton, LLP.

(57) ABSTRACT

A fixation system for a bone conduction device is disclosed. An abutment is coupled to a bone anchor such that vibrations applied to the abutment pass into the bone anchor. The abutment defines a conduction path to the bone anchor such that vibrations applied to the abutment are transferred to the bone anchor. The abutment comprises a plurality of shearing elements disposed adjacent the bone anchor, wherein the shearing elements form part of the conduction path. The fixation system also comprises a vibratory coupler extending from the bone conduction device, comprising a second conduction surface and a magnet, wherein the magnet attracts to the abutment so as to couple the second conduction surface to the abutment, thereby enabling vibrations to pass through the conduction path. The shearing elements are configured to slide laterally in response to tangential forces incident upon the abutment.

30 Claims, 16 Drawing Sheets

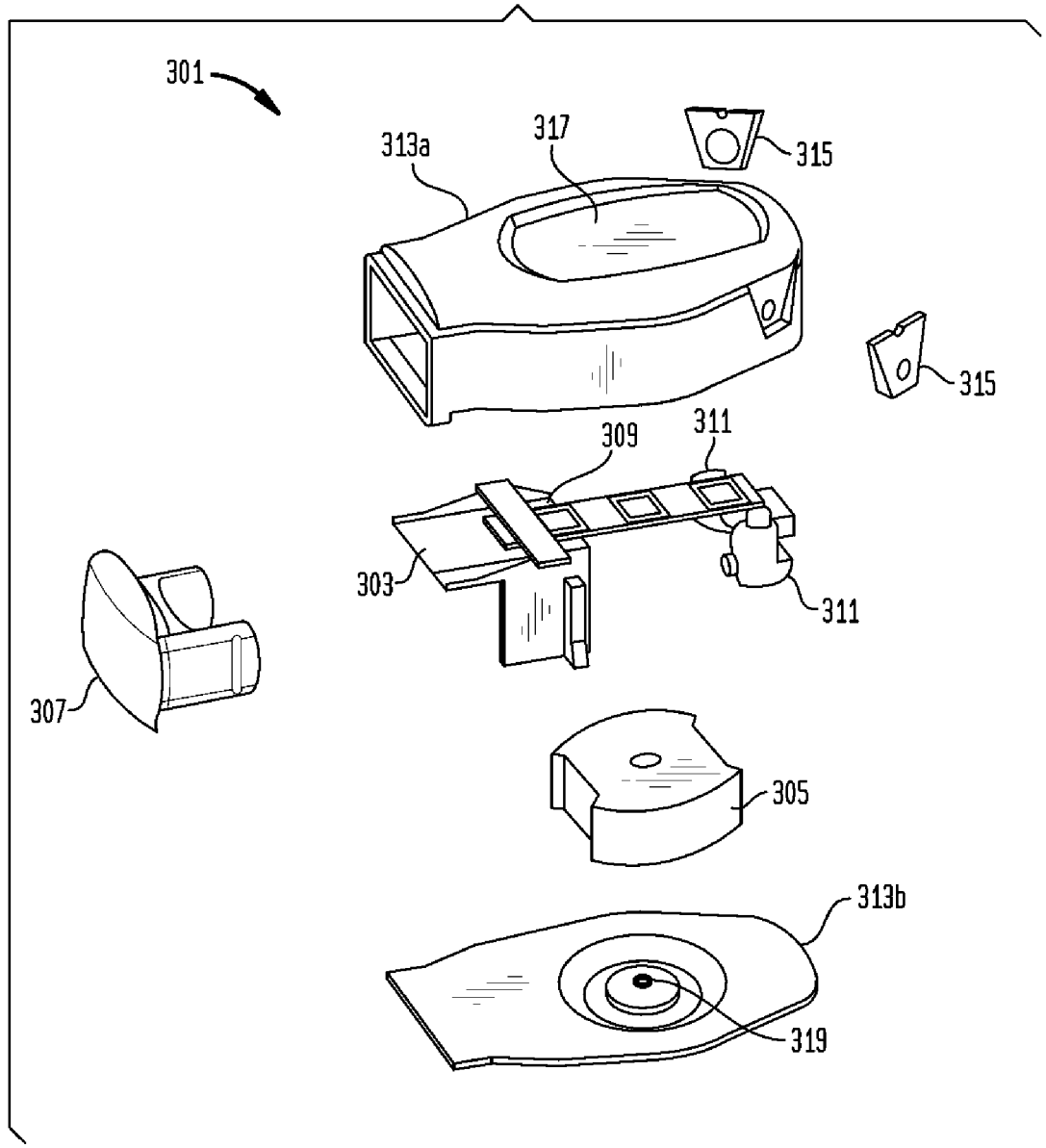

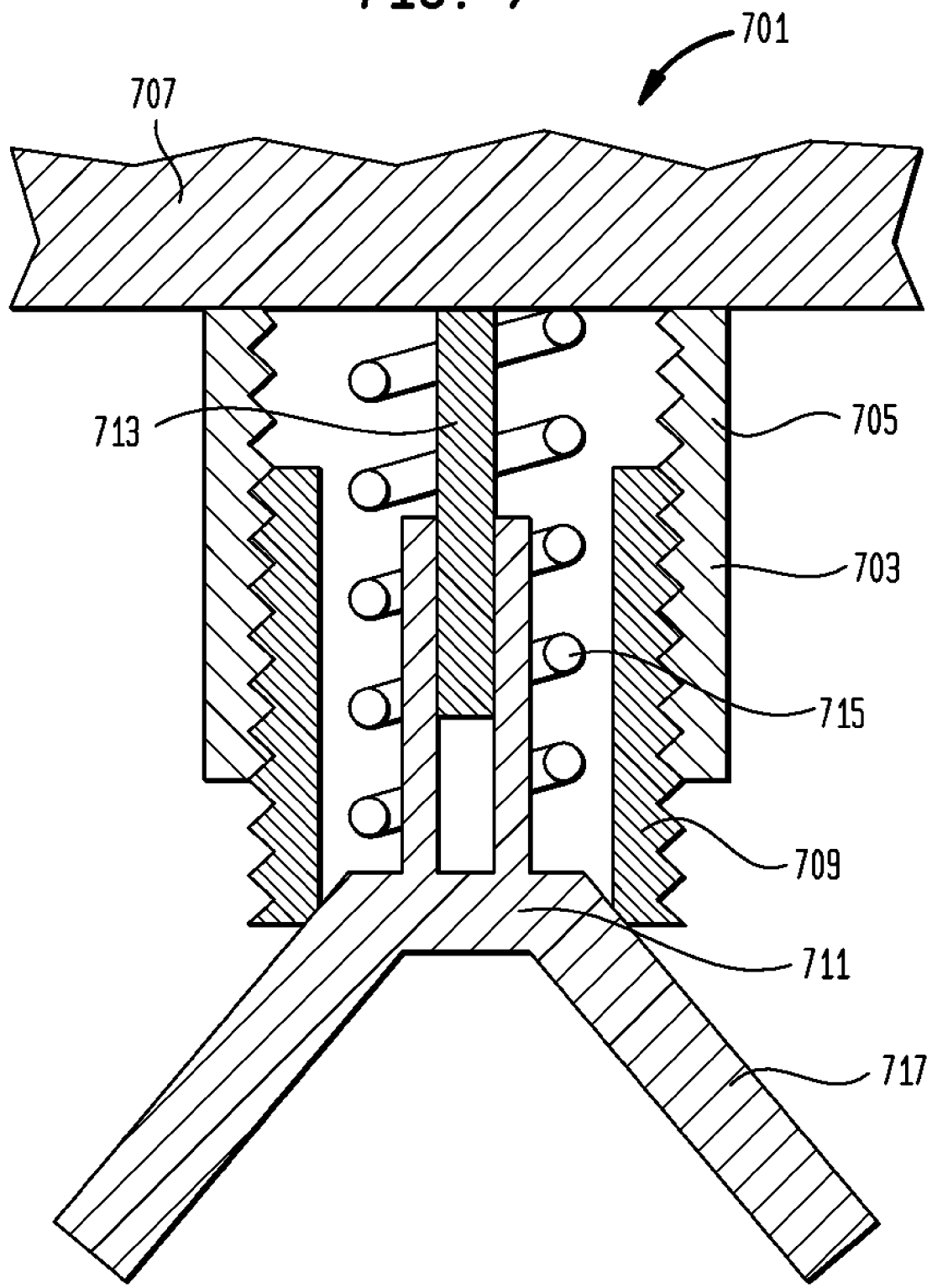

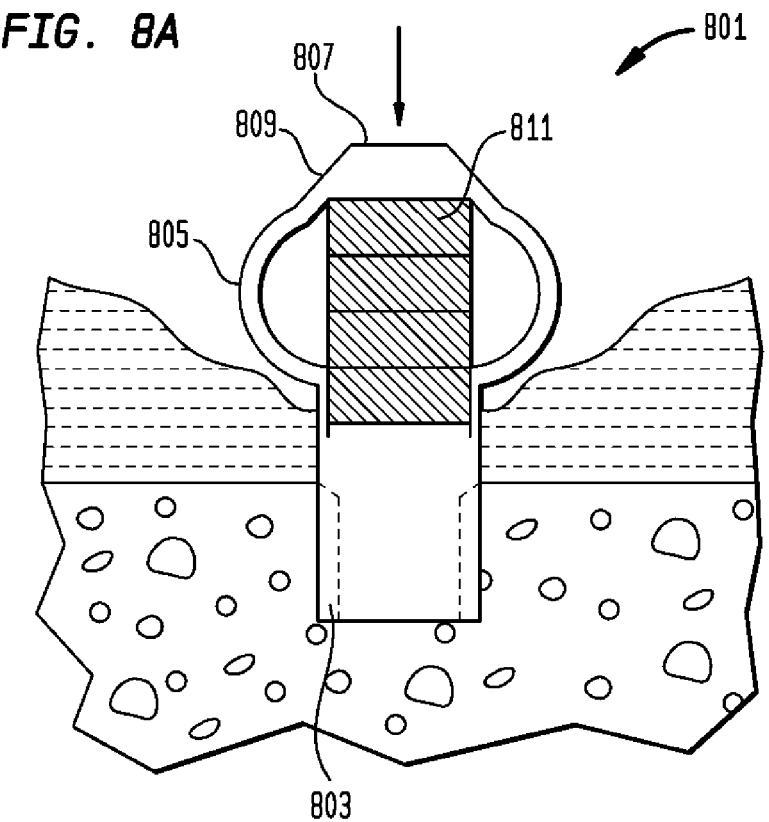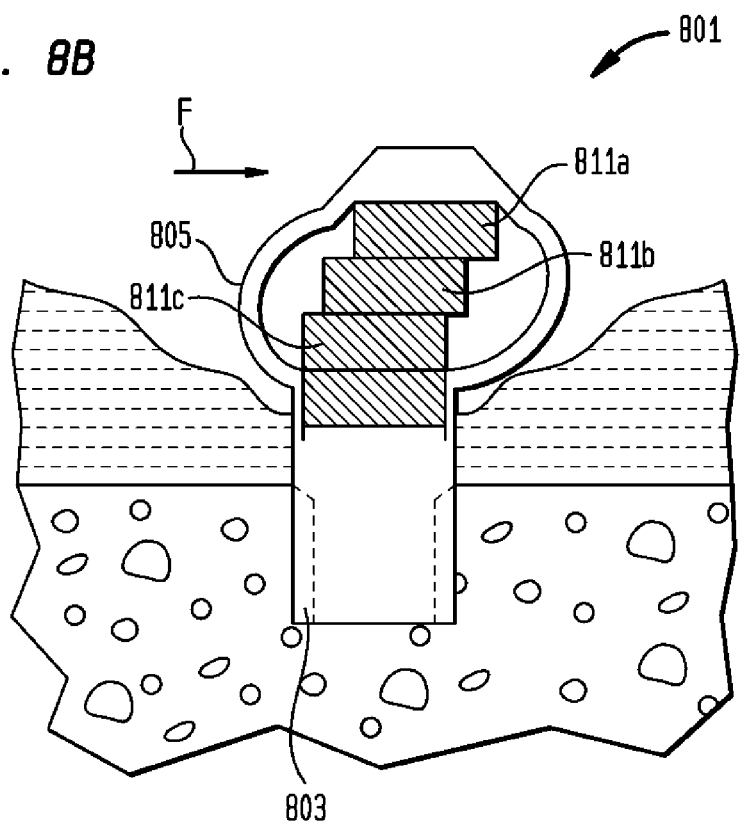

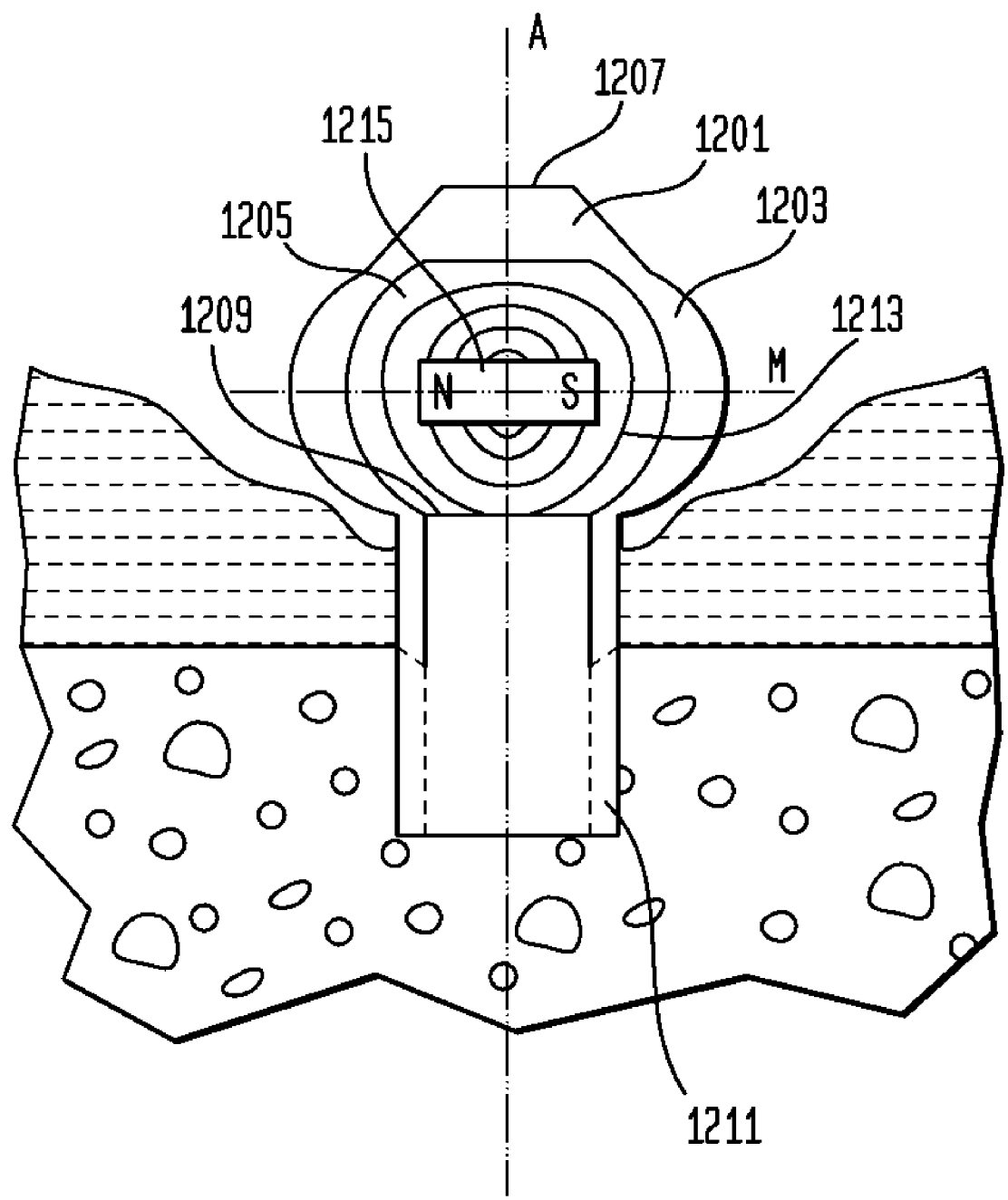

TANGENTIAL FORCE RESISTANT COUPLING FOR A PROSTHETIC DEVICE

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention relates generally to prosthetic devices, and more particularly, to a tangential force resistant coupling for a prosthetic device.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to bypass the mechanisms of the ear. More specifically, an electrical stimulus is provided via the electrode array directly to the cochlea nerve, thereby causing a hearing sensation.

Conductive hearing loss occurs when the normal mechanical pathways to provide sound to hair cells in the cochlea are impeded, for example, by damage to the ossicular chain to ear canal. However, individuals who suffer from conductive hearing loss may still have some form of residual hearing because the hair cells in the cochlea are generally undamaged.

Individuals who suffer from conductive hearing loss are typically not candidates for a cochlear implant due to the irreversible nature of the cochlear implant. Specifically, insertion of the electrode array into a recipient's cochlea results in the destruction of the majority of hair cells within the cochlea. The destruction of the cochlea hair cells results in the loss of all residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Furthermore, hearing aids are typically unsuitable for individuals who suffer from single-sided deafness (total hearing loss only in one ear) or individuals who suffer from mixed hearing losses (ie. Combinations of sensorineural and conductive hearing loss).

These individuals who cannot benefit from hearing aids may benefit from hearing prostheses that use the principles of bone conduction device to provide acoustic signals to a recipient. Such hearing prostheses direct vibrations into the bone, so that the vibrations are conducted into the cochlea and result in stimulation of the hairs in the cochlea. This type of prosthesis is typically referred to as a bone conduction device.

Bone conduction devices function by converting a received sound signal into a mechanical vibration representative of the received sound. This vibration is then transferred to the bone structure of the skull, causing vibration of the recipient's skull. This skull vibration results in motion of the fluid of the cochlea, thereby stimulating the cochlea hair cells and causing a hearing sensation to be perceived by the recipient. Vibration from a bone conduction device is generally conducted to the recipient's cochlea via a screw implanted in the recipient's skull.

The skull bone, at the point of implant of the bone screw, is susceptible to damage from lateral forces on the bone screw, particularly during the healing period following the implant procedure. This healing period varies from person to person, depending upon many factors associated with the patient's overall health and genetics, but generally takes six weeks or more. During the healing period, the bone is so susceptible to damage that the general practice is that the bone conduction device is not coupled to bone screw until the healing period has ended. Further, while the bone is less susceptible to damage following the healing period, damage may still be possible if a large lateral force is applied thereto.

SUMMARY OF THE INVENTION

In accordance with aspects of the present invention, a fixation system for a bone conduction device is provided. The fixation system comprises: a bone anchor configured to be implanted in a recipient; an abutment coupled to the bone anchor defining a conduction path to the bone anchor such that vibrations applied to the abutment are transferred to the bone anchor, wherein the abutment comprises a plurality of shearing elements forming part of the conduction path positioned adjacent the bone anchor; and a vibratory coupler extending from the bone conduction device, comprising a second conduction surface and a magnet, wherein the magnet attracts to the abutment such that the second conduction surface is coupled to the abutment, thereby enabling vibrations to pass through the conduction path, wherein the shearing elements are configured to slide laterally in response to tangential forces incident upon the abutment.

In accordance with other aspects of the present invention, an implantable anchor for coupling to a vibratory coupler extending from a bone conduction device, the vibratory coupler comprising a second conduction surface and a magnet is provided. The implantable anchor comprises: a bone anchor configured to be implanted in a recipient; and an abutment coupled to the bone anchor defining a conduction path to the bone anchor such that vibrations applied to the abutment are transferred to the bone anchor, wherein the abutment comprises a plurality of shearing elements forming part of the conduction path positioned adjacent the bone anchor; wherein when the second conduction surface is substantially adjacent the abutment, the magnet attracts to the abutment such that the second conduction surface is coupled to the abutment, thereby enabling vibrations to pass through the conduction path, wherein the shearing elements are configured to slide laterally in response to tangential forces incident upon the abutment.

BRIEF DESCRIPTION OF THE DRAWINGS

Illustrative embodiments of the present invention are described herein with reference to the accompanying drawings, in which:

FIG. 3 is an exploded view of an external module for a bone conduction device;

FIG. 7 is a sectional view of a second alternative embodiment for the vibratory coupler associated with the external module of a bone conduction device;

FIG. 8A is a sectional view of a first alternative embodiment for the abutment of a bone conduction device;

FIG. 8B illustrates the lateral deformation of the abutment of FIG. 8A;

FIG. 12 is a sectional view of a fourth alternative embodiment for the abutment of a bone conduction device;

DETAILED DESCRIPTION

The present invention is directed toward a fixation system for a prosthetic device, such as bone conduction device. A bone anchor is implanted into the skull, and an abutment is coupled to the bone anchor so as to define a conduction path to the bone anchor such that vibrations applied to the abutment are transferred to the bone anchor. The abutment comprises a plurality of shearing elements disposed adjacent to the bone anchor that form part of the conduction path. The fixation system further comprises a vibratory coupler extending from the bone conduction device, comprising a second conduction surface and a magnet, wherein the magnet attracts to the abutment so as to couple the second conduction surface to the abutment, thereby enabling vibrations to pass through the conduction path. The shearing elements are configured to slide laterally in response to tangential forces incident upon the abutment.

Figure 1:
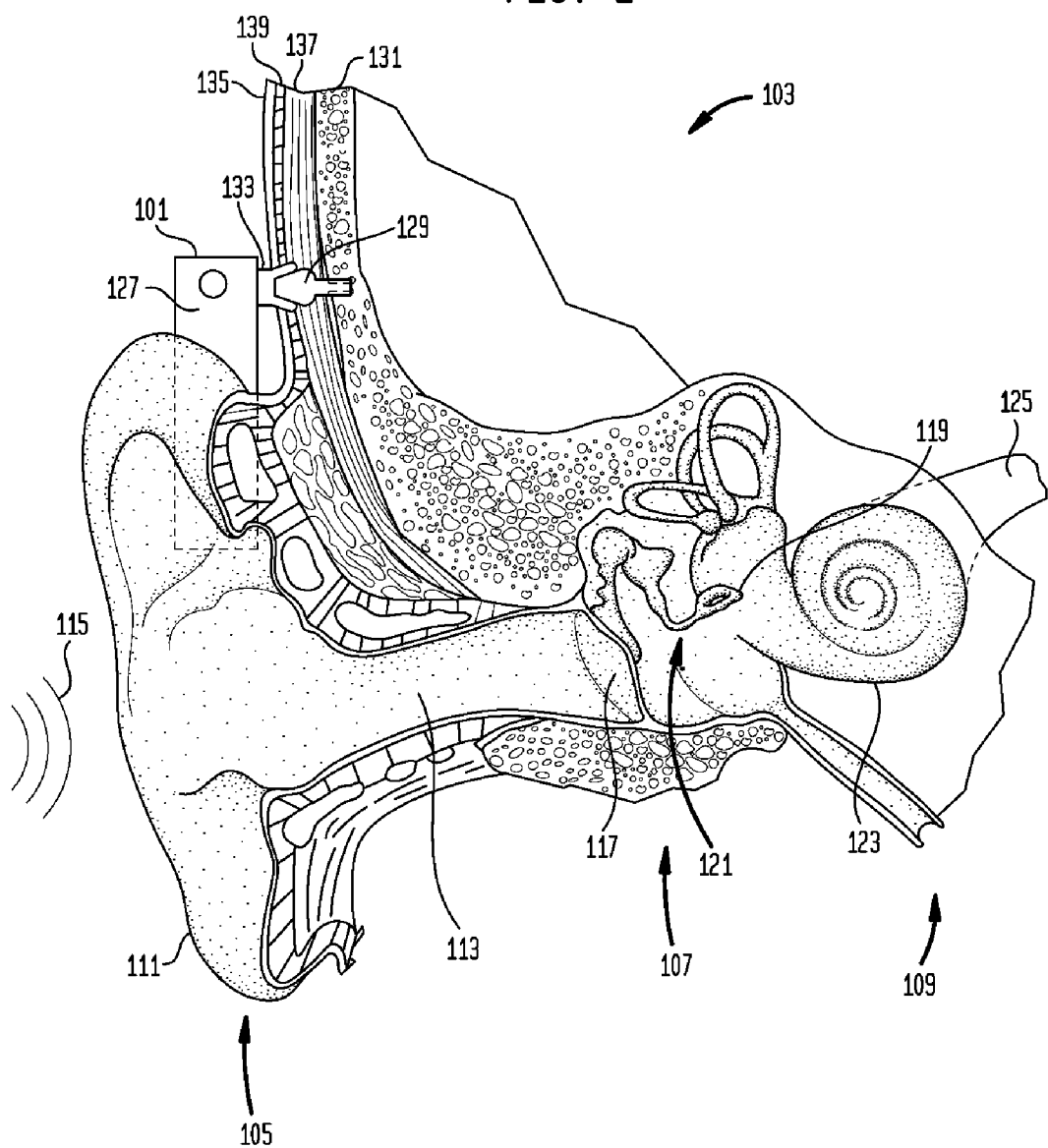
FIG. 1 is a partial sectional view of a skull showing the ear canal, the cochlea, and a bone conduction device with the bone anchor implanted in the skull and the external module coupled to the bone anchor.

FIG. 1 is a perspective view of an exemplary bone conduction device 101 with which embodiments of the present invention may be advantageously implemented. The fully functional human hearing anatomy is generally divided up into the outer ear 105, the middle ear 107, and the inner ear 109. The outer ear 105 includes the auricle 111 and the ear canal 113. Sound waves 115 are collected by auricle 111 and channeled into and through ear canal 113. The tympanic membrane 117, which is located at the boundary between the outer ear 105 and the middle ear 107, vibrates in response to the sound waves 107. Within the middle ear 107, vibration of the tympanic membrane 117 is coupled to the fenestra ovalis 119 through three bones, collectively referred to as the ossicles 121. The ossicles 121 filter and amplify the vibrations, thereby causing the fenestra ovalis 119 to articulate. The movement of the fenestra ovalis 119 generates pressure waves in the fluid within cochlea 123, which in turn induces movement in the hairs lining the inside of the cochlea 123. Movement of the hairs generates nerve impulses in spiral ganglion cells to which the hairs are connected, and those nerve impulses are passed to the auditory nerve 125, and then to the brain (not shown), where they are perceived as sound.

Bone conduction device 101 is shown positioned behind the auricle 111 of the recipient, although the device could also be positioned in a variety of other positions in the skull of the recipient. Bone conduction device 101 includes an external module 127, and is coupled to the skull of the recipient via an implanted anchor, such as bone screw 129. Bone screw 129 is secured to the skull bone 131 during the implant procedure.

As discussed in more detail below, connected to external module 127 is a vibratory coupler 133 which secures external module 127 to bone screw 129. As should be appreciated, any appropriate anchor system may be used in lieu of the bone screw 129, so long as the anchor system conducts sufficient vibrations from the bone conduction device 101 for the recipient to perceive the vibrations as sound. For example, as discussed below, the anchor system may be implanted under skin 135 of the recipient, within muscle tissue 137 and/or fat tissue 139. In addition, the material from which the bone anchor is constructed is a matter of design choice. For example, the material may be a metal that does not stimulate an undesirable response of body systems, or it may be any other type of biocompatible material.

Figure 2:
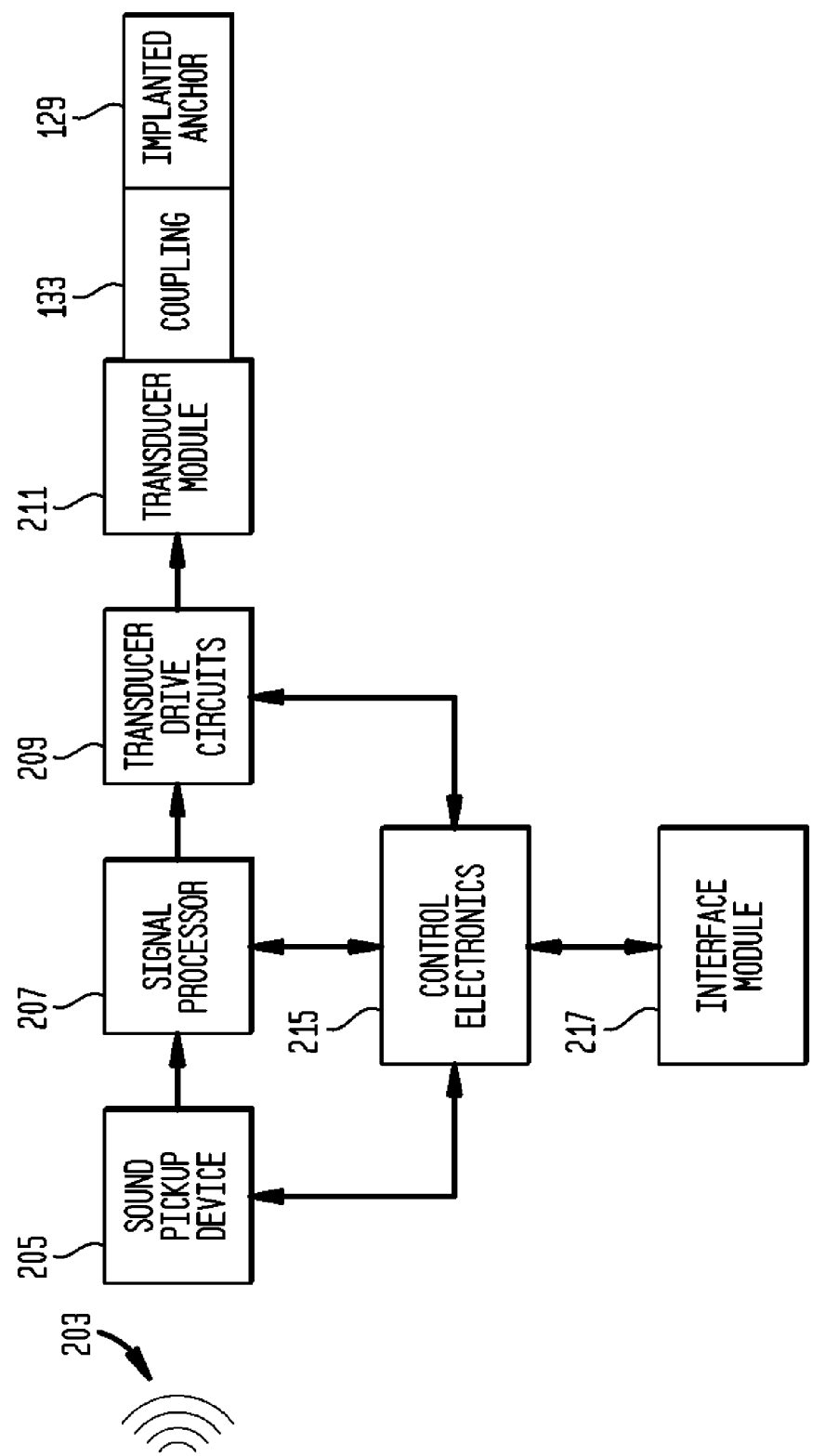
FIG. 2 is a schematic diagram of a bone conduction device.

The sound and signal processing components of external module 127 are schematically shown in FIG. 2. Sound waves 203 are received by a sound pickup device 205 and converted into a representative signal, which is directed into a signal processor 207. Signal processor 207 converts the representative signal into an appropriate signal adjusted, as necessary, for the transducer drive circuit 209, which outputs a drive signal to a transducer module 211. Adjustments to the representative signal may include filtering, removal of distortions, reduction of background noises, and the like. Transducer module 211 generates a mechanical vibration representative of the sound waves 203, and these mechanical vibrations are conducted to the skull via a mechanical coupling between transducer module 211, namely vibratory coupler 133, and bone screw 129. An appropriate power module (not shown) is included as part of the external module to provide power to each of the various components.

A control module 215, having control electronics therein, is electronically connected to sound pickup device 205, signal processor 207, and transducer drive circuit 209. Control module 215 may also be electronically connected to transducer module 211, or any other components of external module 127. Control module 215 monitors and controls operation of the electronic components and circuits to which it is connected. The amount of control provided by control module 215 may vary depending upon the component or circuit type.

Control module 215 may also serve as a feedback loop to provide corrections to the output of any one or more of the components where necessary.

An interface module 217 is connected to control module 215 to permit the recipient, or a skilled practitioner of the medical arts, to adjust preselected settings of external module 127. The preselected settings may include volume, sound processing strategies, power on/off the device, and the like. Optionally, the interface module and the control module may be integrated into a single module.

Those skilled in the art will appreciate that, as a matter of design choice, any of the signals between circuits forming part of external module 127 may be transmitted via a wired connection or wirelessly. Further, not all circuits need be housed within a single casing.

Signal processor 207 may use one or more different techniques or strategies to selectively process, amplify, and/or filter the signal representative of sound waves 203. In certain embodiments, signal processor 207 may be of substantially the same as the sound processor that is used in an air conduction hearing aid. As another option, signal processor 207 may include and analog to digital converter and a digital signal processor.

FIG. 3 illustrates an exploded view of one embodiment of an external module of a bone conduction device, referred to herein as external module 301. External module 301 shown in FIG. 3 includes an electronics module 303, a transducer module 305, and a battery shoe 307 for powering the electronic components. Electronics module 303 and the transducer module 305 operate as described above. Electronics module 303 includes a printed circuit board 309 (PCB) to electrically connect and mechanically support the various electronic components and circuits. One or more microphones 311 are directly attached to PCB 309 to function as sound pickup devices. Alternatively, other types of direct audio input could be used as the sound pickup devices instead of, or in addition to, microphones 311. Such alternatives include digital or analog audio input ports, a telecoil, and the like.

The housing for the external module 301 includes a top part 313a and a bottom part 313b. The two housing parts 313a, 313b are configured to mate with one another, leaving an opening for insertion of battery shoe 307. Following insertion of battery show 307, housing parts 313a, 313b substantially seal the internal components of external module 301 from external elements. The top housing part 313a includes one or more snap-on microphone covers 315, which protect the microphones 311 from dust, dirt and other debris. A user interface 317 is disposed on one side of the top housing part 313A to give the recipient access to the interface module 217 functions.

The bottom housing part 313b includes an opening 319 for insertion of a fastener (not shown). The fastener secures transducer module 305 to the inside of the bottom housing part 313b, and/or secures a vibratory coupler, such as one of the vibratory couplers shown below, to the outside of the bottom housing part 313b and/or transducer module 305. As such, a direct mechanical connection is established for conduction of vibrations from the transducer module 305 to the vibratory coupler, and from there into the bone anchor. Once the fastener is in place, opening 319 may be sealed against external elements by use of an o-ring or other sealant.

Figure 4A:
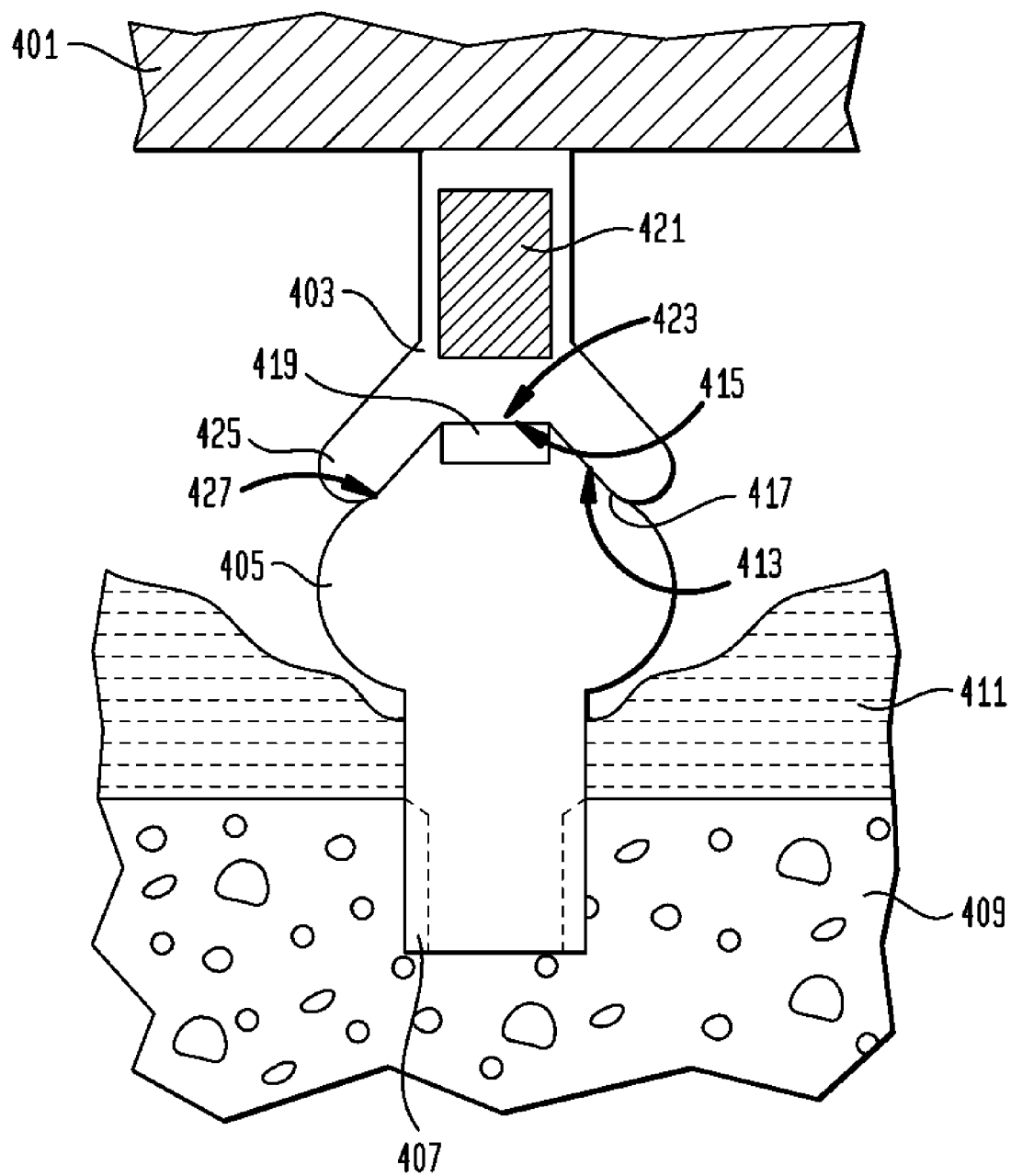
FIG. 4A is a partial sectional view of a fixation system for a bone conduction device.

FIG. 4 illustrates a coupling system in accordance with embodiments of the present invention. As shown, the coupling system comprises a vibratory coupler 403 and an implanted anchor system. In the illustrated embodiment, vibratory coupler 403 extends from an external module 401, sometimes referred to herein as a vibration generating module 401, and is coupled to the implanted anchor system. The implanted anchor system comprises an abutment 405 and an anchor 407, such as bone screw 407. Abutment 405 may be releasably affixed to bone screw 407.

As shown, abutment 405 extends above tissue 411 so that vibratory coupler 403 may be seated on abutment 405. As discussed below, the combination of vibratory coupler 403, abutment 405, and bone screw 407 enable vibrations from external module 401 to be conducted into bone 409.

Those skilled in the art will recognize that alternate configurations for a bone anchor may also be used instead of the bone screw. One such example is a plate secured to the bone in at least two locations along the edge of the plate, such that the center portion of the plate rests against or is mechanically coupled to the skull bone, thereby enabling vibrations applied to the bone anchor to pass into the bone. With such a bone anchor, the abutment may extend from the center portion of the plate, and forces normal to the skull incident upon the abutment or the external module would not impact a surgically modified site, but rather would impact an unaltered section of the skull bone.

The top portion of the abutment 405, which extends above the tissue 411, has a regularly defined cross-section, and may be circular, elliptical, or any other shape according to design preferences. In addition, the radius about the entire cross-section need not be constant. A constant radius may be used in circumstances where it is desired to allow the external module to be mounted with any orientation. On the other hand, a non-constant radius may be used in circumstances where the external module is intended to have only a single orientation when the vibratory coupler is seated on the abutment.

In the illustrated embodiment, abutment 405 comprises a bearing surface 413 of which extends away from a conduction surface 415. Bearing surface 413 extends away from conduction surface such that an acute angle, or at least a non-orthogonal angle, is formed along the surface of abutment 405. The shapes of bearing surface 413 and the conduction surface 415 are a matter of design choice, however, the conduction surface is preferably planar to facilitate coupling with vibratory coupler 403 and conduction of vibrations. Alternatively, if bearing surface 413 is curved, the bearing surface and conduction surface 415 may intersect tangentially.

In the illustrated embodiments, as bearing surface 413 extends away from conduction surface 415, a shelf 417 is formed in the bearing surface. The particular geometry of this shelf 417 may vary according to other design considerations, particularly the geometry of vibratory coupler 403. Optionally, and again depending upon the geometry of vibratory coupler 403, shelf 417 may be entirely omitted from abutment 405. In certain embodiments, as shown in FIG. 4, abutment 405 also includes a magnetic material 419 set into the abutment 405 at conduction surface 415. This magnetic material 419 may form part of conduction surface 415, or alternatively, it may be disposed beneath the surface. Moreover, the magnetic material may have any geometrical configuration that suits other design choices that are made concerning abutment 405 and vibratory coupler 403. Magnetic material 419 is preferably magnetizeable material, and not a permanent magnet, although a permanent magnet could be used.

As noted, vibratory coupler 403 extends outward from external module 401 and includes a magnet 421. Vibratory coupler 403 further includes a conduction surface 423, and a leveraging extension 425. Conduction surface 423 of vibratory coupler 403 has a complimentary shape to conduction surface 415 of abutment 405, and seats directly on the conduction surface of the abutment such that mechanical contact is made between the two conduction surfaces 415, 423. Magnet 421 in vibratory coupler 403 interacts with the magnetic material 419 in the abutment 405 to retain the two conduction surfaces 415, 423 seated together under normal use conditions. The holding force generated between magnet 421 and magnetic material 419 should be sufficient to maintain the seating under the force generated by the weight of vibratory coupler 403. In addition, the holding force should also be sufficient to maintain the seating when the instantaneous force generated by vibrations from external module 401 are coupled with the weight of vibratory coupler 403.

Leveraging extension 425 extends away from conduction surface 423 of vibratory coupler 403 such that at least a distal edge 427 of the leveraging extension seats upon the bearing surface 413, and preferably upon shelf 417. Optionally, the entire inner surface of leveraging extension 425 may seat on bearing surface 413. The configuration of the leveraging extension 425 may vary widely. For example, the leveraging extension may form an annular ring at the distal end, or alternatively, the annular ring may be divided up into two, four, or more sections, each section connected to the main body of the vibratory coupler via an arm. In another alternative, the leveraging extension may be a plurality of arms extending away from the main body of the vibratory coupler. In such an embodiment, more arms are preferable, however, as few as two arms will generally suffice.

Figure 4B:
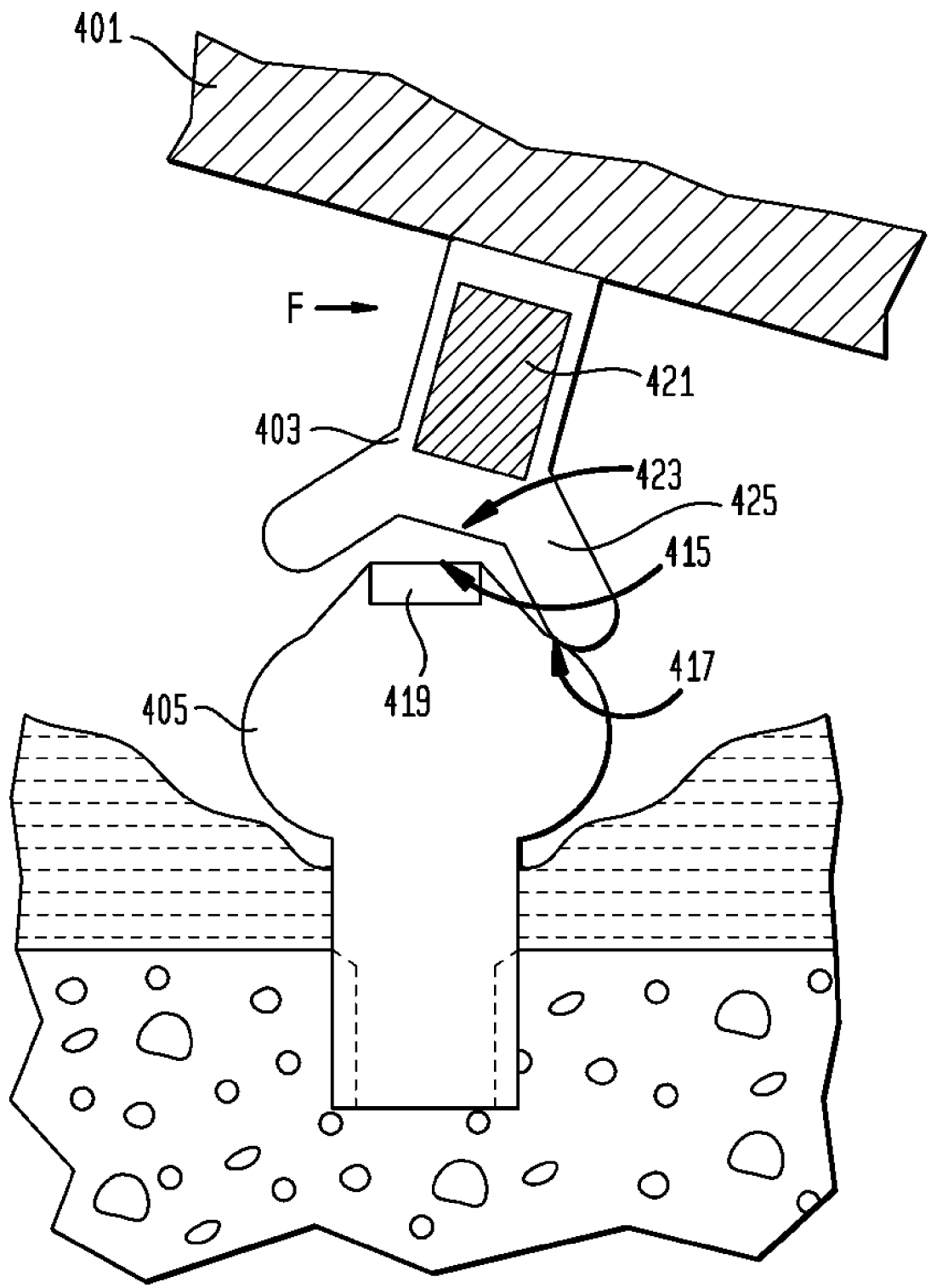
FIG. 4B illustrates the vibratory coupler pivoted on the abutment for the bone conduction device of FIG. 4A.

FIG. 4B illustrates how the vibratory coupler 403 is decoupled from abutment 405 when a part of the external module 401 is subjected to a force that is tangential to the skull. The tangential force is marked by the arrow, F, and upon incidence of this tangential force on external module 401, conduction surface 423 of the vibratory coupler 403 is pivoted up and away from the conduction surface 415 of abutment 405. This pivoting action is caused by the leveraging extension 425 seated upon the shelf 417 of abutment 405 on the opposite side of vibratory coupler 403 from where the force is incident. Upon application of the force, F, leveraging extension 425 acts as a lever arm, and assists in lifting and magnetically decoupling magnet 421 from magnetic material 419. By causing the decoupling in this manner, the amount of tangential force to which abutment 405 is subjected is significantly reduced.

Figure 5:
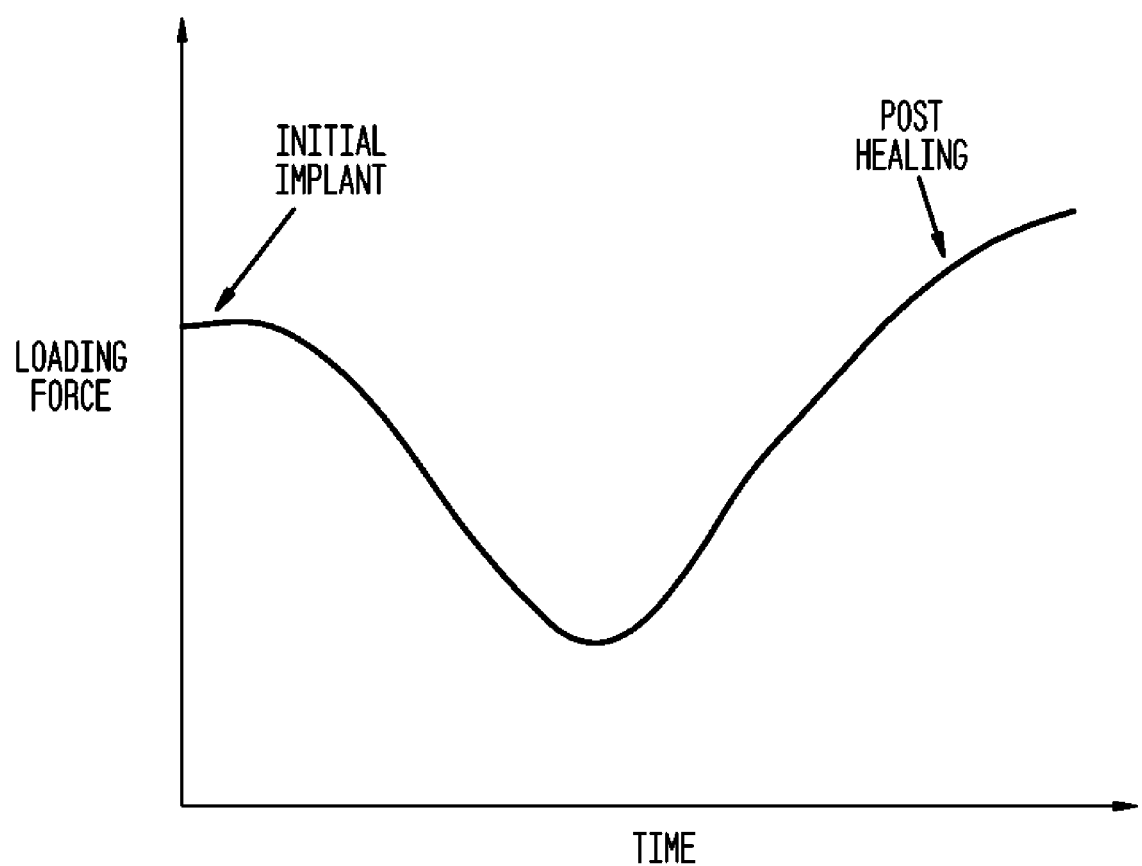
FIG. 5 is a graph illustrating the longitudinal loading force curve for a bone screw set into the skull bone as the bone heals over time.

The amount of tangential force to which a bone screw may be subjected following implantation, without causing damage to the bone, is illustrated in FIG. 5. Initially, when a bone screw is implanted, the amount of tangential loading force to which it may be subjected is somewhat high. As the healing process begins and continues, the amount of tangential force to which a bone screw may be subjected significantly decreases and then begins increasing to a level that is higher than at the stage of the initial implant. The decrease is at least partially due to the fact that when bones are damaged, the human body first breaks down some of the bone structure surrounding the damaged site before beginning to rebuild and heal the bone. Thus, following implantation of a bone screw, until a physician determines that the implant site is fully healed, if there is significant risk of damaging the bone at the implant site by wearing the external module, then the external module is not generally worn. For prior art bone conduction devices, this is how implant patients proceed—they refrain from regularly using the external module until healing is complete. With the bone conduction fixation system described above, it is anticipated that the external module may be seated upon and used with the implanted bone screw almost immediately following the implant procedure and continuing through the entire healing process.

Figure 6:
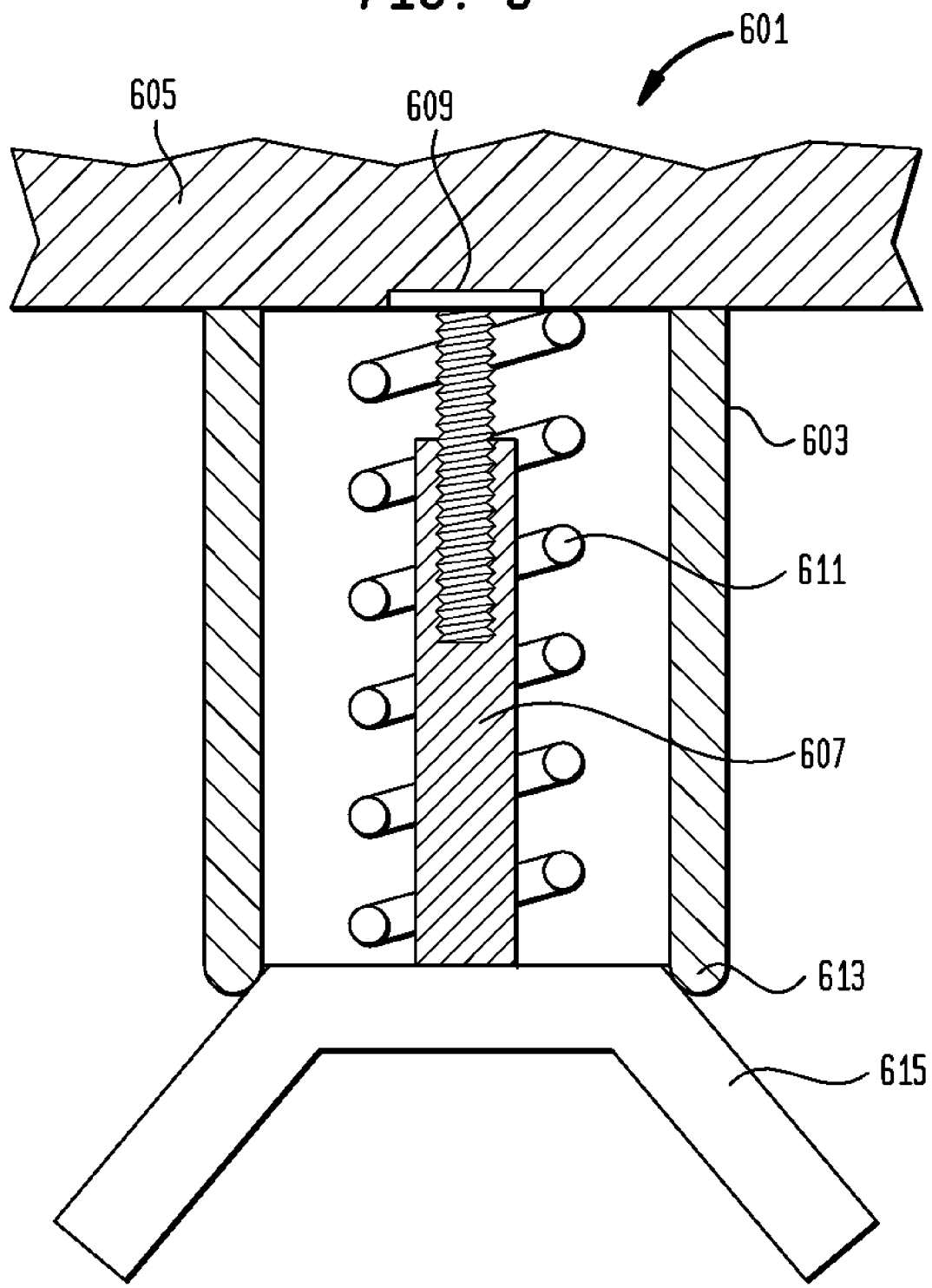
FIG. 6 is a sectional view of a first alternative embodiment for the vibratory coupler associated with the external module of a bone conduction device.

An alternative embodiment of a vibratory coupler in accordance with embodiments of the present invention is shown in FIG. 6. In the illustrated embodiment, a sheath 603 extends from housing 605 of external module 601. A coupling arm 607 is partially disposed within sheath 603. Coupling arm 607 is held to the body of external module 601 via a fastener 609, which enables the position of coupling arm 607 relative to housing 605 to be adjusted. A spring 611 is also included within sheath 603 and biases against adjustments made by the fastener 609. As the position of the coupling arm 607 is adjusted, the distal edges 613 of the sheath 603 exert pressure on leveraging extension 615 to cause constriction. By constricting leveraging extension 615, some variation may be introduced in the amount of tangential force required to unseat the vibratory coupler from the abutment, thereby enabling a custom fit for any particular implant recipient.

FIG. 7 illustrates another embodiment of a vibratory coupler 701 in accordance with embodiments of the present invention. As shown, vibratory coupler 701 includes a sheath 703 is formed of two parts, a first part 705 which extends from body 707 of external module 701, and a second part 709 which is threaded into first part 705. With this arrangement, the overall length of the sheath 703 is adjustable. Similar to the embodiments described above, coupling arm 711 extends into sheath 703. However, as shown, a post 713 extends from body 707, and the coupling arm 711 slidingly fits onto post 713. A spring 715 disposed within sheath 703 biases the coupling arm 711 toward body 707 of external module 701. Here, constriction of leveraging extension 717 is enabled by lengthening sheath 707 and biasing the coupling arm into the sheath by use of spring 715. Conversely, the amount of constriction may be reduced by shortening sheath 707.

FIG. 8 illustrates alternative embodiments for an abutment in accordance with embodiments of the present invention, referred to as abutment 801. As described below, Abutment 801 further reduces the amount of tangential force to which the bone screw 803, or other bone anchor, might be subjected.

Abutment 801 comprises an outer sheath 805 which includes a conduction surface 807 and a bearing surface 809 as described above with reference to FIGS. 4A and 4B. Outer sheath 805 may be constructed of thin walled titanium, or other similar material, which can be laser welded to the bone screw to ensure that the interface between the outer sheath and the bone screw is smooth and does not provide crevices for the lodgment of debris. Outer sheath 805 is constructed to house a plurality of shearing elements, in this case, several stacked plates 811. The plates 811 are not connected to one another, and each may slide laterally with respect to adjacent plates. The plates 811 do not need to be similarly dimensioned. To facilitate sliding, the surfaces of the plates 811 may be polished, or alternatively, a lubricant may be included within outer sheath 805. Further, the material from which plates 811 are constructed is a matter of design choice. For example, they may be constructed from a light weight plastic or polymer material, a biocompatible material, or a heavier metal material. In addition, the plates may be constructed from a magnetizeable material, but preferably not from material that is a permanent magnet, as such a construction is likely to significantly inhibit lateral sliding between adjacent plates.

Outer sheath 805 serves at least a few purposes in this embodiment. First, outer sheath 805 maintains each plate 811 within the stack in physical contact with each adjacent plate to ensure that abutment 805 is mechanically stiff in a direction normal to the skull. By maintaining such contact, and thereby keeping the stack of plates 805 mechanically stiff, the stack conducts vibrations from conduction surface 807 through to bone screw 803. Additionally, contact between plates 811 keep each plate from laterally sliding with respect to adjacent plates under normal use conditions. Another purpose of outer sheath 805 is to limit lateral sliding of the plates 811 so that a conduction path is maintained to pass vibrations from the external module to the bone screw 803. Yet another purpose of the outer sheath 805 is to assist in returning plates 811 to the default stack configuration following deformation of the stack when subjected to lateral forces.

FIG. 8B shows the stack of plates 811 with the top two plates 811a, 811b laterally displaced as a result of a lateral force F. Outer sheath 805 deforms along with the stack of plates 811. To enable outer sheath 805 to return the plates to the default stack configuration, outer sheath 805 may be formed from a shape memory material. Alternatively, springs may be included within outer sheath 805 to aid in biasing the stack of plates 811 toward the default stack configuration. Non-permanent magnets, strategically placed within each stacked plate, could also be used to aid in realignment of the stacked plates into the default stack configuration.

Figure 9A:
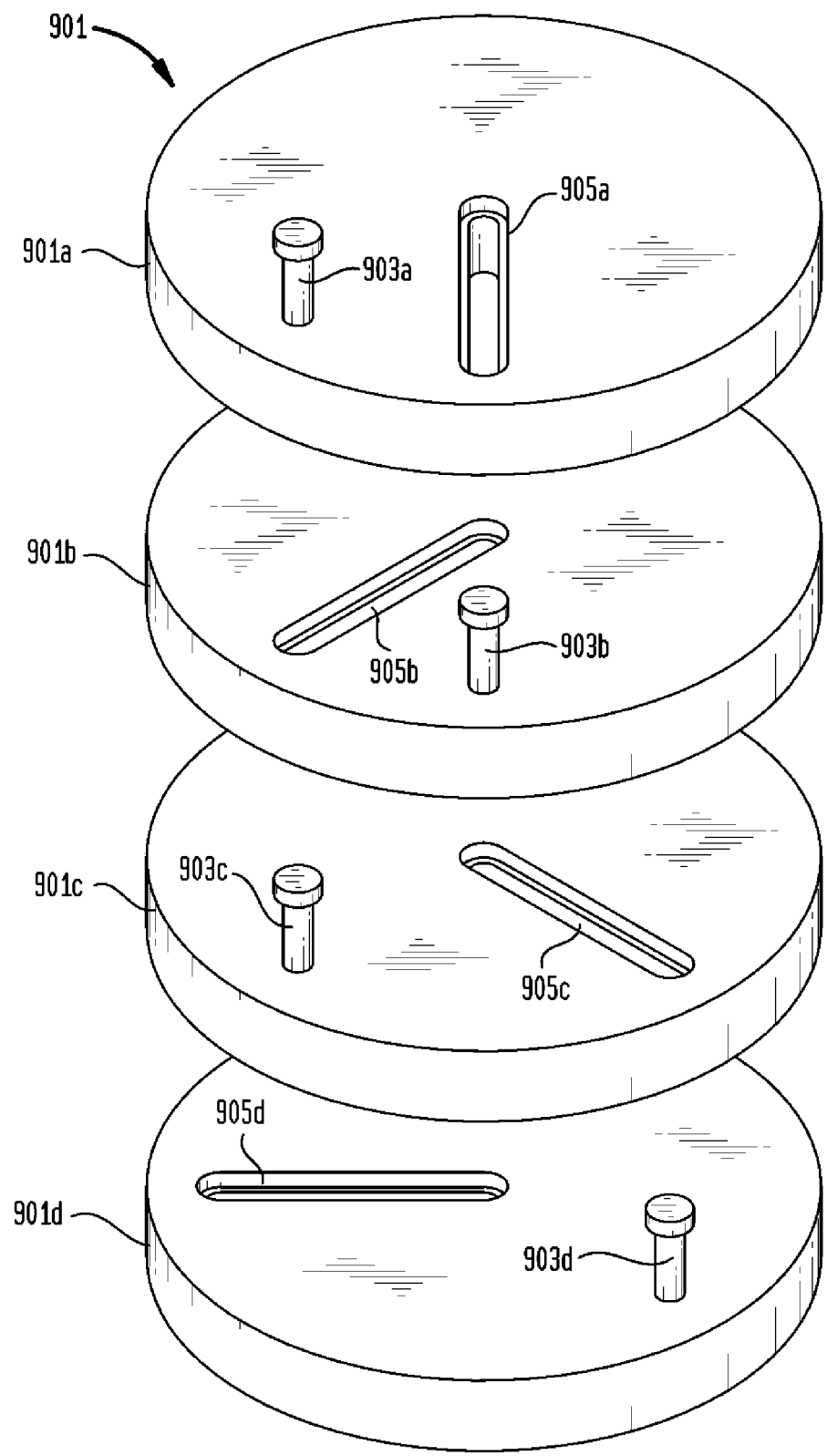
FIG. 9A is a perspective view of a first alternative embodiment for shearing elements associated with the abutment.
Figure 9B:
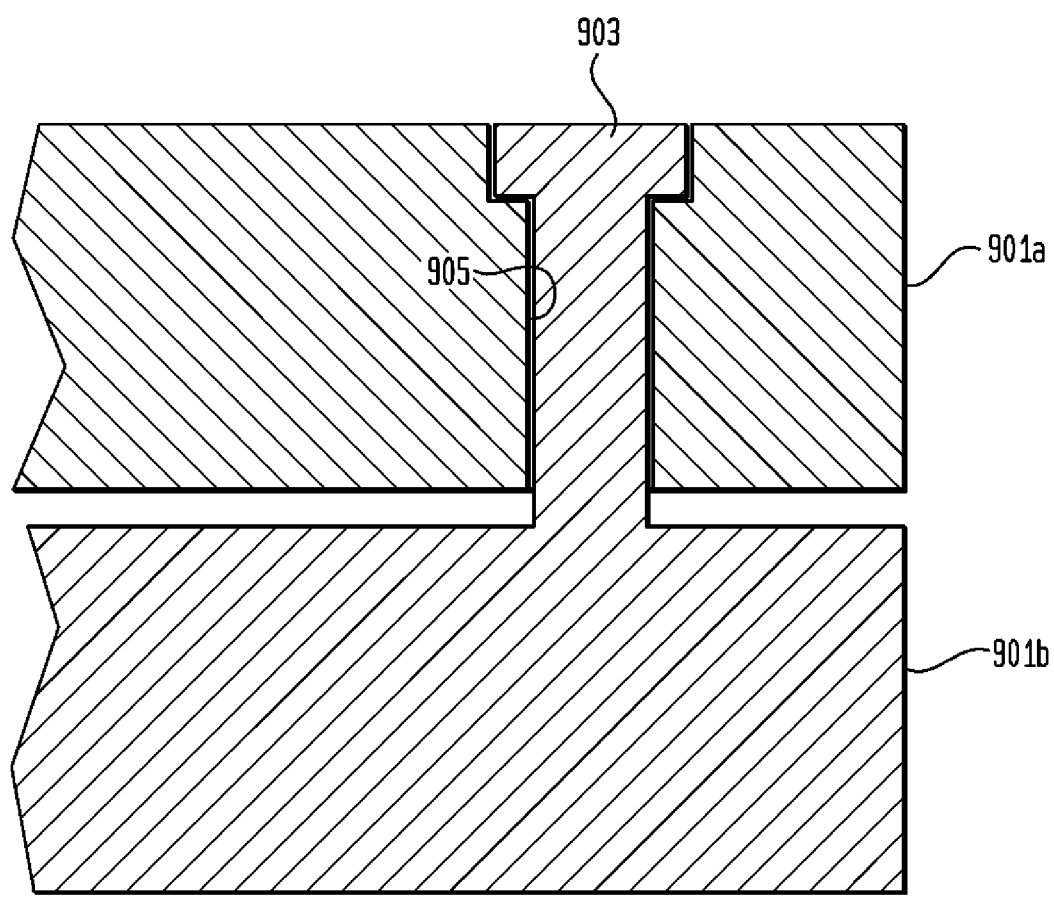
FIG. 9B illustrates a sectional view of the coupling between shearing elements of FIG. 9A.

FIG. 9A shows an alternative arrangement for a plurality of stacked plates 901 which may be used in accordance with embodiments of the present invention. In the illustrated embodiment, each plate is interlocked with adjacent plates. Each plate 901a-d includes an outward extending pin 903 and a slot 905. Plates 901a-d are stacked so that pin 903a-d of each plate 901a-d is inserted into the slot 905a-d of an adjacent plate. The pin 903 of each plate seats within the slot 905 of an adjacent plate as shown in FIG. 9B. The pin 903a on the end plate 901a (as shown), having only a single adjacent plate, may either be omitted from the construction or used for another purpose—lacking an adjacent plate, the pin 903 of the end plate 901a is not inserted into a corresponding slot. As shown, the slot 905a-d in each plate 901a-d is curved, so that when the stack 901 is subjected to a lateral force, displacement of any one or more plates will also cause rotation of the displaced plates. Such rotation helps to further absorb any incident lateral forces. Because the plates are interlocked, and an outer sheath is not required, although one may be used. Moreover, this embodiment might also be implanted subcutaneously. Such a subcutaneous abutment would necessarily couple with the external module through the skin of the recipient, and all vibrations would be transmitted through tissues, including skin, covering the implant. The pin of the end plate may be used to assist with the coupling.

Figure 10:
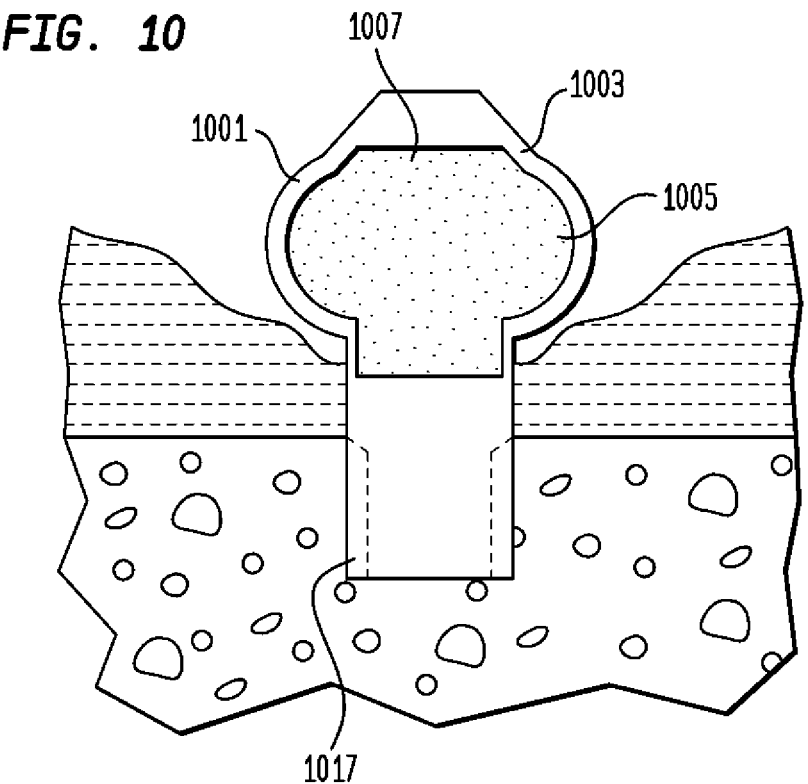
FIG. 10 is a sectional view of a second alternative embodiment for the abutment of a bone conduction device.

Yet another alternative embodiment of an abutment in accordance with embodiments of the present invention is illustrated in FIG. 10. In the illustrated embodiment, abutment 1001 comprises an outer sheath 1003 having an internal cavity 1005 and a granulated material 1007 disposed therein. The granulated material 1007 may any number of different types of material, from sand, to magnetizeable particles, to small beads, whether plastic, glass, or metal and the like. In the case of magnetizeable particles, it is anticipated that the magnet within the external module would align the particles to assist in forming a conduction path between the conduction surface and the bone anchor, while at the same time permitting shearing action between the particles in response to lateral forces incident upon the outer sheath. Additional materials may be included within the cavity to either better enable shearing action of the granulated particles, i.e., movement in the lateral direction in response to lateral forces incident upon the abutment, or to better enable conduction of vibrations from the external module, through the granulated material, to the bone anchor. For example, collagen may be included within the internal cavity, along with beads, to better aid in the transmission of vibrations. It is anticipated that collagen might also aid in improving the shearing action of such beads. As with the previous embodiment, the outer sheath may be constructed using a shape memory material to aid in returning the abutment to a default shape.

Figure 11:
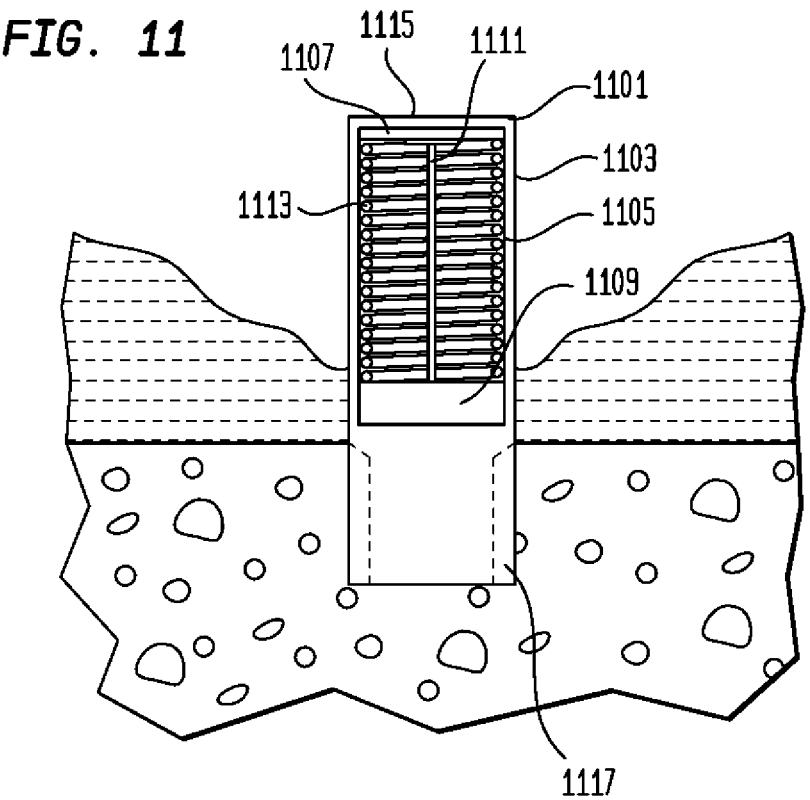
FIG. 11 is a sectional view of a third alternative embodiment for the abutment of a bone conduction device.

Another embodiment of an abutment in accordance with embodiments of the present invention is illustrated as abutment 1101 in FIG. 11. This abutment includes an outer sheath 1103 with an external profile which is a matter of design choice. Outer sheath 1103 may be formed as shown, it may be formed according to any of the other embodiments discussed herein, or it may have an entirely different shape to suit other design considerations. Outer sheath forms an internal cavity 1105, in which is disposed a proximal plate 1107, a distal plate 1109, a wire 1111, which forms a flexible conduction path, and a spring 1113. The proximal plate 1107 is disposed adjacent to, and may be coupled to, the conduction surface 1115 of outer sheath 1103 such that vibrations applied to conduction surface 1115 pass through to distal plate 1109. Similarly, the distal plate 1109 is disposed adjacent and coupled to bone anchor 1117. The wire 1111 extends between and is coupled to both proximal plate 1107 and distal plate 1109. Likewise, spring 1113 is disposed between proximal and distal plates 1107, 1109, but spring 1113 biases the plates 1107, 1109 away from one another, thereby placing the wire 1111 under tension and enabling the wire 1111 to conduct vibrations applied to proximal plate 1107 through to the proximal plate 1109, and thus in to the bone anchor 1117.

Additional wires may be included to form additional conduction paths. The material from which the wire or wires is constructed is a matter of design choice. Those skilled in the art will recognize that certain materials, such as metals and other materials that are less susceptible to permanent deformation due to stretching, are better suited for long term use within the abutment. Those materials that are susceptible to permanent deformation due to stretching may still be used, but abutments employing such materials may require more frequent replacement.

Yet another embodiment of an abutment 1201 is shown in FIG. 12. In the illustrated embodiment, abutment 1201 includes an outer sheath 1203 forming an internal cavity 1205. As with other embodiments, outer sheath 1203 is preferably constructed using a shape memory material to provide some flexibility, but at the same time be sufficiently rigid to seat a vibratory coupler. Outer sheath 1203 includes a conduction surface 1207 and a distal surface 1209 which is coupled to bone anchor 1211, and vibrations applied to distal surface 1209 are conducted into bone anchor 1211. A conduction axis, A, defines the conduction path along which vibrations pass from an external module to bone anchor 1211 once the external module is seated on the abutment. A spiral spring 1213 and a magnet 1215 are disposed within the cavity 1205. The spiral spring 1213 has an outer end coupled to distal surface 1209, and the magnet 1215 is coupled to the center end of the spiral spring. The magnet 1215 has a magnetic axis, M, defined by the two magnetic poles, N and S, and the spiral spring 1213 biases the magnet 1215 so that the magnetic axis is not parallel to, and is preferably perpendicular to, the conduction axis A. When the vibratory coupler is seated on abutment 1201, a magnet within the vibratory coupler, as described in FIG. 4, induces magnet 1215 in abutment 1201 to rotate and align magnetic axis, M, with the conduction axis, A. Once the magnet 1215 in the abutment 1201 rotates, it is attracted toward the magnet in the vibratory coupler. In addition, magnet 1215 in abutment 1201 will seat against distal surface 1209, thereby enabling vibrations applied to abutment 1201 to pass through to bone anchor 1211.

Thus, a fixation system for a bone conduction device is disclosed. While embodiments of this invention have been shown and described, it will be apparent to those skilled in the art that many more modifications are possible without departing from the inventive concepts herein. The invention, therefore, is not to be restricted except in the spirit of the following claims.

Figure 13A:
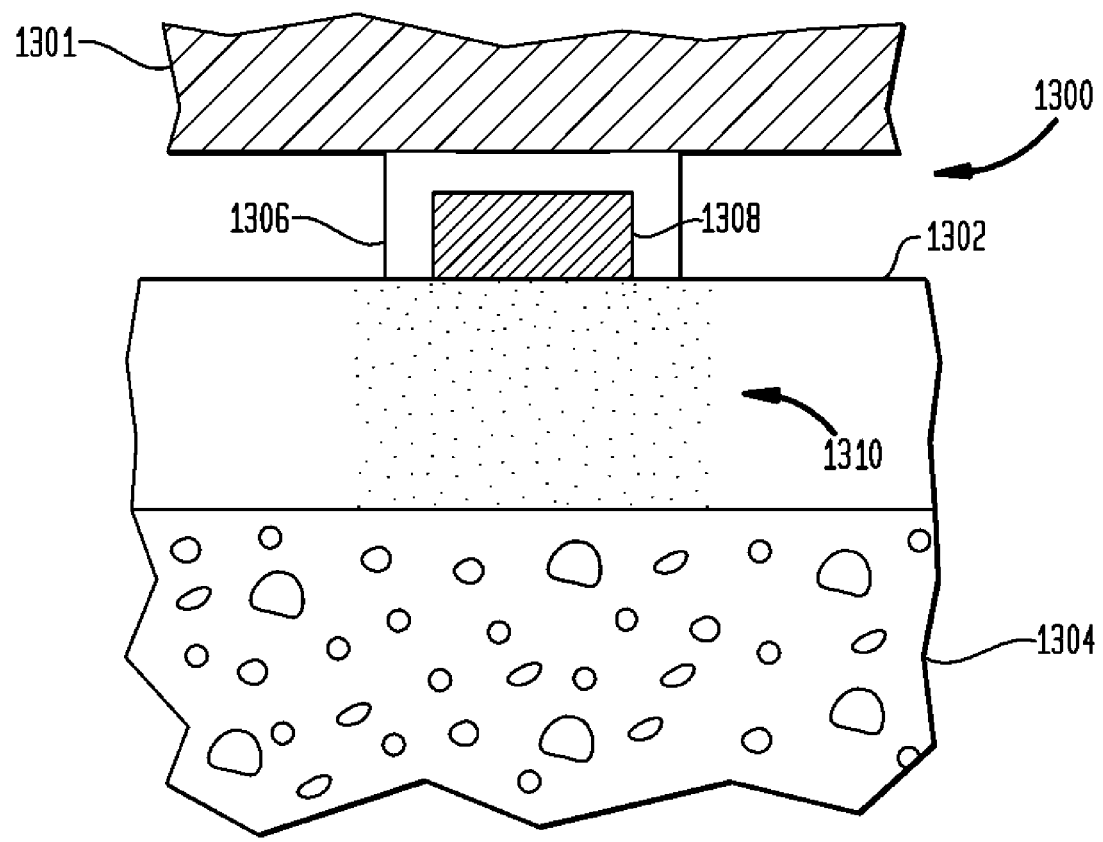
FIG. 13A is cross-sectional view of a coupling system in accordance with embodiments of the present invention.

FIG. 13A is cross-sectional view of a coupling system in accordance with embodiments of the present invention. As shown, the coupling system comprises a vibratory coupler 1306 attached to, and extending from, an external module 1301 of a bone conduction device. Disposed within vibratory coupler 1306 is a magnet 1308. Implanted within skin 1302 is an implanted anchor 1310. Vibration generated by external module 1301 is coupled through implanted anchor 1310 to the skull 1304.

In the illustrated embodiments, implanted anchor 1310 comprises a plurality of particles, beads, or other elements 1310 which are injected or implanted into skin 1302. The plurality of particles 1310 alter the material stiffness of the skin so that the vibration from vibrator coupler 1306 may be transferred to the skull 1304 with little to no loss, thus eliminating the need for an exposed abutment.

Any of a variety of particles may be injected or implanted into skin 1302 of a recipient. In certain embodiments, skin 1302 is stiffened by injecting a sufficient quantity of ceramic or metallic powder (e.g., titanium powder, platinum powder, etc) into the skin. In other embodiments, collagen or any other bioresorable material that may provide stiffness to skin 1302 may be used. For example, in certain embodiments, particles that enhance fibrous tissue growth may be injected or implanted into skin 1302.

As noted, in the illustrated embodiment, a magnet 1308 is disposed within vibratory coupler 1306. Magnet 1308 is configured to provide an attraction force between vibratory coupler 1306 and particles 1310. This attraction retains external module 1301 in position during normal use, and is sufficient to attach external module 1301 to the recipient under the force generated by the weight of vibratory coupler 1306. In addition, the attraction force should also be sufficient to maintain the attachment when the instantaneous force generated by vibrations from external module 1301 are coupled with the weight of vibratory coupler 1306. In certain embodiments, magnet 1308 may comprise a permanent magnet. In other embodiments, magnet 1308 may comprise a magnetic material that is not a permanent magnet.

In further embodiments, particles 1310 are prevented from migrating from the injection site. In one such embodiment, the particles may be tied to one another prior to injection/implantation. In another such embodiment, the particles may be coated with collagen to prevent migration. Other particles comprising, such as silicone particles, may promote tissue in-growth there with to prevent migration.

Figure 13B:
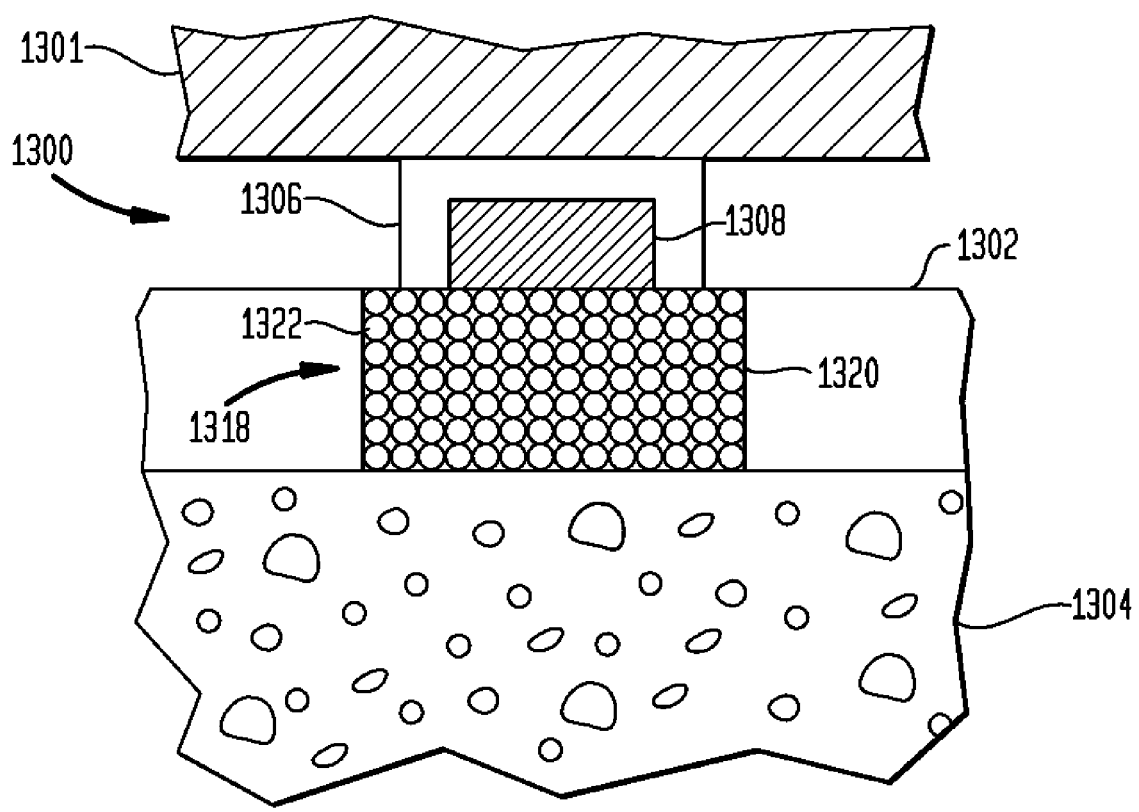
FIG. 13B is cross-sectional view of a coupling system in accordance with embodiments of the present invention.

FIG. 13B is cross-sectional view of a coupling system in accordance with embodiments of the present invention. In this embodiment, implanted anchor 1318 comprises a granulated material 1322 bounded by a volume 1320. The granulated material 1322 may any number of different types of material, from sand, to magnetizeable particles, to small beads, whether plastic, glass, or metal and the like. Volume 1320 may comprise, for example, a surgically implanted mesh or cage 1320 which prevents migration of granulated material 1322.

Similar to the embodiments described above with reference to FIG. 13A, a magnet 1308 is disposed within vibratory coupler 1306. Magnet 1308 is configured to provide an attraction force between vibratory coupler 1306 and particles 1310. This attraction retains external module 1301 in position during normal use, and is sufficient to attach external module 1301 to the recipient under the force generated by the weight of vibratory coupler 1306. In addition, the attraction force should also be sufficient to maintain the attachment when the instantaneous force generated by vibrations from external module 1301 are coupled with the weight of vibratory coupler 1306. In certain embodiments, magnet 1308 may comprise a permanent magnet. In other embodiments, magnet 1308 may comprise a magnetic material that is not a permanent magnet.

Figure 13C:
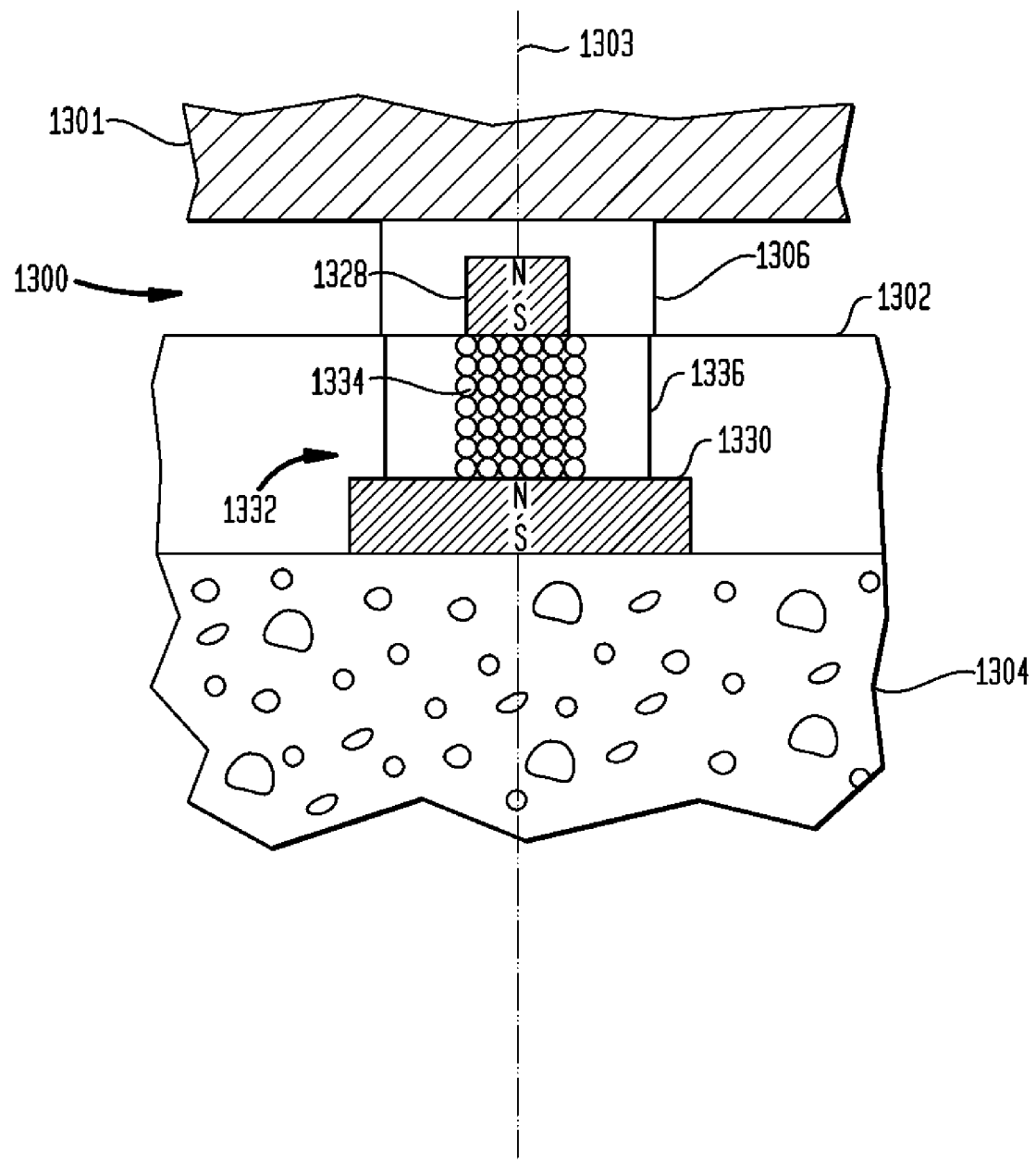
FIG. 13C is cross-sectional view of a coupling system in accordance with embodiments of the present invention.

FIG. 13C is cross-sectional view of a coupling system in accordance with embodiments of the present invention. Similar to the embodiments described above with reference to FIG. 13B, a granulated material 1334 bounded by a volume 1336. The granulated material 1322 may any number of different types of material. Implanted anchor 1332 further comprises a magnet 1330 adjacent skull 1304. Vibratory coupler 1306 comprises a permanent magnet 1328. When vibratory coupler 1306 is positioned adjacent skin 1302, magnets 1330 and 1328 cause granulated material 1334 to be substantially aligned, thereby improving the transmission of vibration therethrough.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A fixation system for a bone conduction device comprising:
    a bone anchor configured to be implanted in a recipient;
    an abutment coupled to the bone anchor defining a conduction path to the bone anchor such that vibrations applied to the abutment are transferred to the bone anchor, wherein the abutment comprises a plurality of shearing elements forming part of the conduction path positioned adjacent the bone anchor; and
    a vibratory coupler extending from the bone conduction device, comprising a second conduction surface and a magnet, wherein the magnet attracts to the abutment such that the second conduction surface is coupled to the abutment, thereby enabling vibrations to pass through the conduction path,
    wherein the shearing elements are configured to slide laterally in response to tangential forces incident upon the abutment.

2. The fixation system of claim 1, wherein the abutment further comprises:
    a first conduction surface; and
    a magnetic material at or near the first conduction surface, wherein the magnet attracts to the magnetic material.

3. The fixation system of claim 1, wherein the abutment further comprises:
    a deformable sheath disposed over the plurality of shearing elements.

4. The fixation system of claim 3, wherein the deformable sheath is adapted to maintain each shearing element in contact with adjacent shearing elements.

5. The fixation system of claim 1, wherein the shearing elements comprising granular particles.

6. The fixation system of claim 5, wherein the granular particles comprise a magnetic material.

7. The fixation system of claim 1, wherein each shearing element is interconnected with adjacent shearing elements such that lateral sliding between adjacent shearing elements is limited.

8. The fixation system of claim 1, wherein the shearing elements comprise a plurality of stacked plates, each stacked plate being adapted to slide laterally with respect to each adjacent stacked plate.

9. The fixation system of claim 1, wherein the abutment further comprises one or more elements disposed therein to facilitate sliding of adjacent shearing elements.

10. The fixation system of claim 1, wherein the abutment further comprises a bearing surface and a first conduction surface that are formed as part of the deformable sheath.

11. The fixation system of claim 10, wherein the bearing surface is adjacent to the first conduction surface and intersects the first conduction surface at a non-orthogonal angle.

12. The fixation system of claim 10, wherein the vibratory coupler further comprises a leveraging extension, and wherein when the second conduction surface is seated on the first conduction surface at least a distal edge of the leveraging extension seats upon the bearing surface.

13. The fixation system of claim 10, wherein the bearing surface and the first conduction surface have different radii of curvatures.

14. The fixation system of claim 1, wherein the first conduction surface is substantially planar.

15. The fixation system of claim 10, wherein the bearing surface comprises a shelf on which the leveraging extension seats when the second conduction surface is seated on the first conduction surface.

16. An implantable anchor for coupling to a vibratory coupler extending from a bone conduction device, the vibratory coupler comprising a second conduction surface and a magnet, the implantable anchor comprising:
   a bone anchor configured to be implanted in a recipient; and
   an abutment coupled to the bone anchor defining a conduction path to the bone anchor such that vibrations applied to the abutment are transferred to the bone anchor, wherein the abutment comprises a plurality of shearing elements forming part of the conduction path positioned adjacent the bone anchor;
   wherein the implantable anchor is configured such that when the second conduction surface is substantially adjacent the abutment, the magnet attracts to the abutment such that the second conduction surface is coupled to the abutment, thereby enabling vibrations to pass through the conduction path, and
   wherein the shearing elements are configured to slide laterally in response to tangential forces incident upon the abutment.

17. The anchor of claim 16, wherein the abutment further comprises:
   a first conduction surface; and
   a magnetic material at or near the first conduction surface, wherein the magnet attracts to the magnetic material.

18. The anchor of claim 16, wherein the abutment further comprises:
   a deformable sheath disposed over the plurality of shearing elements.

19. The anchor of claim 18, wherein the deformable sheath is adapted to maintain each shearing element in contact with adjacent shearing elements.

20. The anchor of claim 16, wherein the shearing elements comprising granular particles.

21. The anchor of claim 20, wherein the granular particles comprise a magnetic material.

22. The anchor of claim 16, wherein each shearing element is interconnected with adjacent shearing elements such that lateral sliding between adjacent shearing elements is limited.

23. The anchor of claim 16, wherein the shearing elements comprise a plurality of stacked plates, each stacked plate being adapted to slide laterally with respect to each adjacent stacked plate.

24. The anchor of claim 16, wherein the abutment further comprises:
   one or more elements disposed therein to facilitate sliding of adjacent shearing elements.

25. The anchor of claim 16, wherein the abutment further comprises:
   a bearing surface and a first conduction surface that are formed as part of the deformable sheath.

26. The anchor of claim 25, wherein the bearing surface is adjacent to the first conduction surface and intersects the first conduction surface at a non-orthogonal angle.

27. The anchor of claim 25, wherein the vibratory coupler further comprises a leveraging extension, and wherein when the second conduction surface is seated on the first conduction surface at least a distal edge of the leveraging extension seats upon the bearing surface.

28. The anchor of claim 25, wherein the bearing surface and the first conduction surface have different radii of curvatures.

29. The anchor of claim 16, wherein the first conduction surface is substantially planar.

30. The anchor of claim 27, wherein the bearing surface comprises a shelf on which the leveraging extension seats when the second conduction surface is seated on the first conduction surface.

* * * * *